(12) United States Patent
Chen

(10) Patent No.: US 7,087,091 B1
(45) Date of Patent: Aug. 8, 2006

(54) ARTIFICIAL KNEE JOINT HAVING A MINIMUM KNEE ANGLE

(76) Inventor: Sen-Jung Chen, No. 236, Sec. 3, Ho-Ping W. Rd., Taipei City (TW)

( * ) Notice: Subject to any disclaimer, the term of this patent is extended or adjusted under 35 U.S.C. 154(b) by 0 days.

(21) Appl. No.: 11/296,682

(22) Filed: Dec. 7, 2005

(51) Int. Cl.
*A61F 2/68* (2006.01)
(52) U.S. Cl. .................................................. 623/44
(58) Field of Classification Search ............. 623/43–45
See application file for complete search history.

(56) References Cited

U.S. PATENT DOCUMENTS

| | | | | |
|---|---|---|---|---|
| 4,451,939 A * | 6/1984 | Thompson | .................... | 623/40 |
| 5,800,566 A * | 9/1998 | Gramnas | ........................ | 623/39 |
| 5,921,358 A * | 7/1999 | Gramnas | ..................... | 188/294 |
| 6,752,835 B1 * | 6/2004 | Shen | ............................. | 623/44 |
| 2005/0038523 A1 * | 2/2005 | Cheng | ........................... | 623/44 |
| 2005/0240129 A1 * | 10/2005 | Daiju | ........................... | 602/16 |

* cited by examiner

*Primary Examiner*—Bruce E. Snow
(74) *Attorney, Agent, or Firm*—Frommer Lawrence & Haug LLP; Ronald R. Santucci

(57) ABSTRACT

An artificial knee joint includes a knee seat attached to a residual thigh, a support frame attached to a prosthetic lower leg, and a driving member disposed pivotally in a mounting recess in the knee seat. A cushion device is disposed between the knee seat and the driving member. Two links have lower ends connected pivotally to the support frame. Two pivot pins extend respectively through upper ends of the links, and are journalled respectively within two mounting holes in the driving member by two bearing members, at least one of which is configured as a unidirectional bearing. When a knee angle is equal to a threshold angle, a pin-locking member is disposed in a pin-locking position so as to prevent rotation of the pivot pins within the driving member and, thus, relative rotation between the knee seat and the support frame.

6 Claims, 9 Drawing Sheets

ARTIFICIAL KNEE JOINT HAVING A MINIMUM KNEE ANGLE

BACKGROUND OF THE INVENTION

1. Field of the Invention

This invention relates to an artificial knee joint, and more particularly to an artificial knee joint having a knee angle that is formed between a residual thigh and a prosthetic lower leg and that is no smaller than a threshold angle.

2. Description of the Related Art

Referring to FIG. 1, a conventional artificial knee joint includes a linkage 10, a knee seat 11 connected to a residual thigh, and a pneumatic cylinder for dampening downward movement of the knee seat 11. The pneumatic cylinder includes a piston rod 12 and a cylinder body 13 connected to a prosthetic lower leg. When the user walks down a slope, the center of gravity of the user may move rearwardly and downwardly within a very short time. If this occurs, it is possible for the piston rod 12 to be moved instantly and rapidly relative to the cylinder body 13, which may results in the user falling down.

SUMMARY OF THE INVENTION

The object of this invention is to provide an artificial knee joint that can prevent the user from falling down when instantly shifting his or her center of gravity rearwardly and downwardly at the start of a downward slope.

According to this invention, an artificial knee joint includes a knee seat attached to a residual thigh, a support frame attached to a prosthetic lower leg, and a driving member disposed pivotally in a mounting recess in the knee seat. A cushion device is disposed between the knee seat and the driving member. Two links have lower ends connected pivotally to the support frame. Two pivot pins extend respectively through upper ends of the links, and are journalled respectively within two mounting holes in the driving member by two bearing members, at least one of which is configured as a unidirectional bearing. When a knee angle is equal to a threshold angle, a pin-locking member is disposed in a pin-locking position so as to prevent rotation of the pivot pins within the driving member and, thus, relative rotation between the knee seat and the support frame. As such, when the user walks down a slope such that the knee angle is reduced to the threshold angle, since relative rotation between the knee seat and the support frame is prevented, the knee angle is maintained at the threshold angle. This prevents the user from falling down when instantly shifting his or her center of gravity rearwardly and downwardly.

BRIEF DESCRIPTION OF THE DRAWINGS

These and other features and advantages of this invention will become apparent in the following detailed description of a preferred embodiment of this invention, with reference to the accompanying drawings, in which.

DETAILED DESCRIPTION OF THE PREFERRED EMBODIMENT

Figure 1:
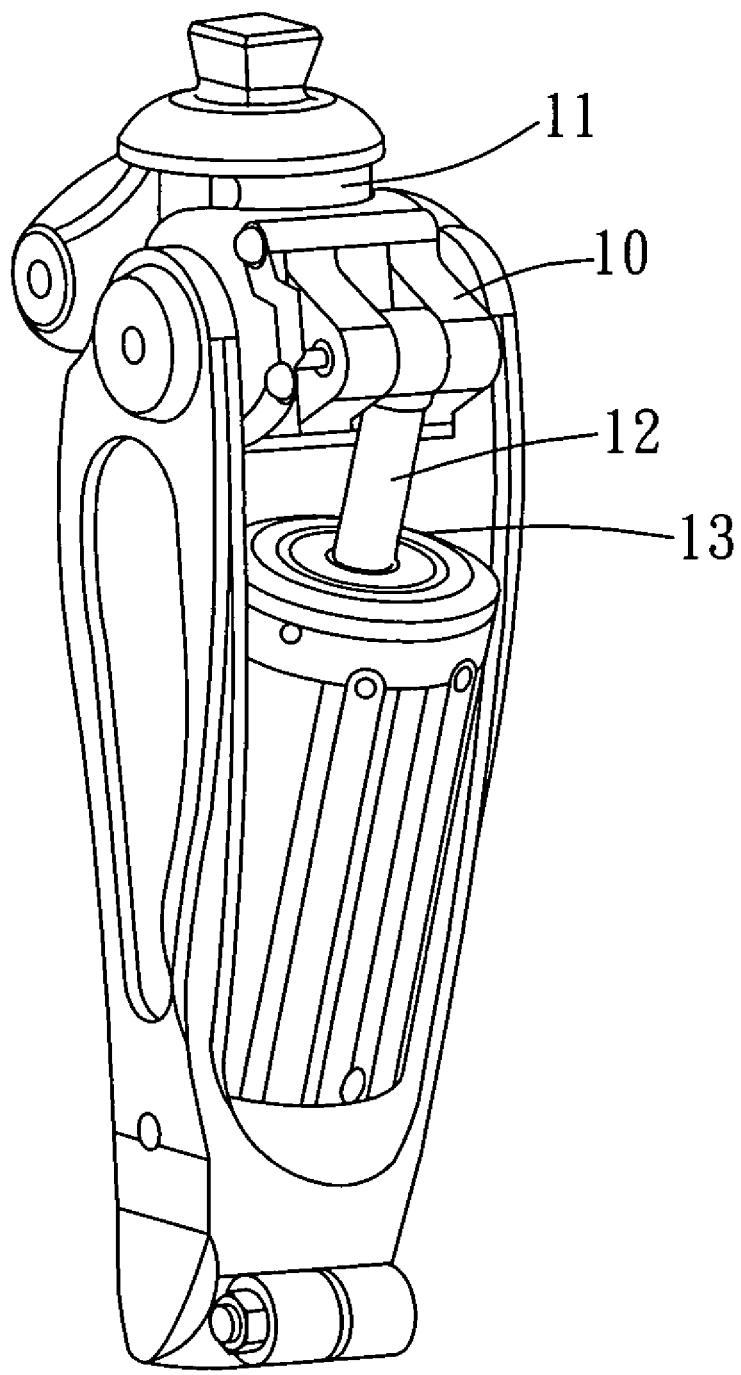
FIG. 1 is a perspective view of a conventional artificial knee joint.
Figure 2:
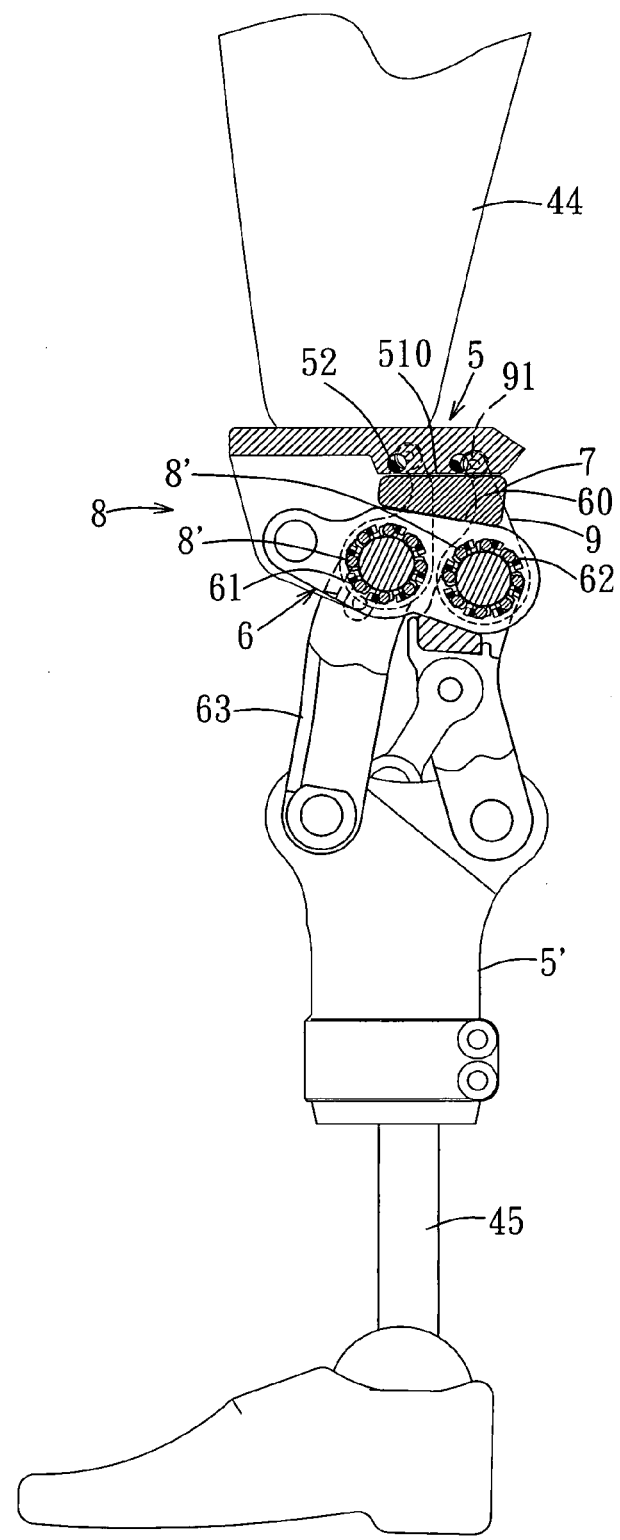
FIG. 2 is a partly sectional schematic view of the preferred embodiment of an artificial knee joint according to this invention.
Figure 3:
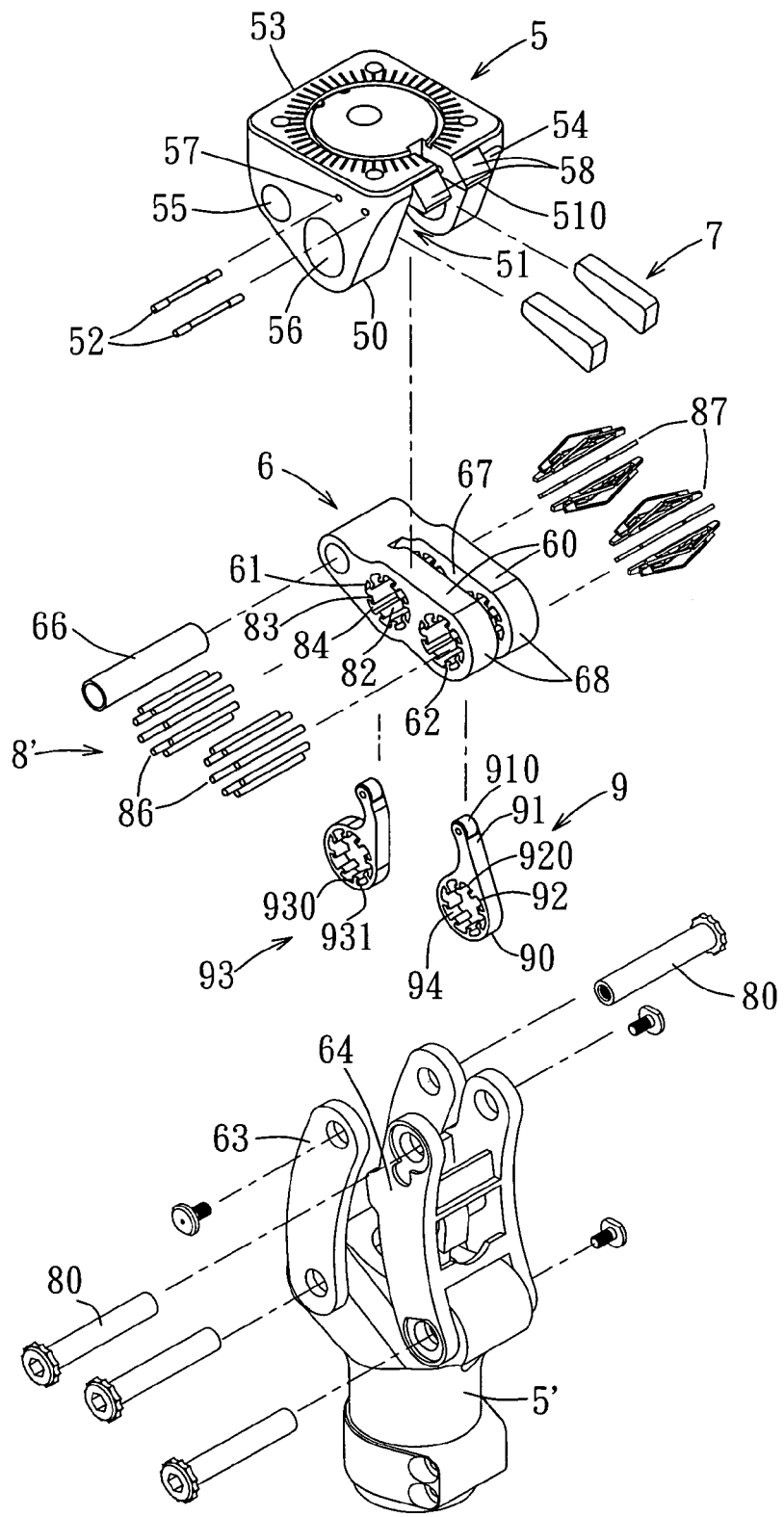
FIG. 3 is an exploded perspective view of the preferred embodiment.
Figure 4:
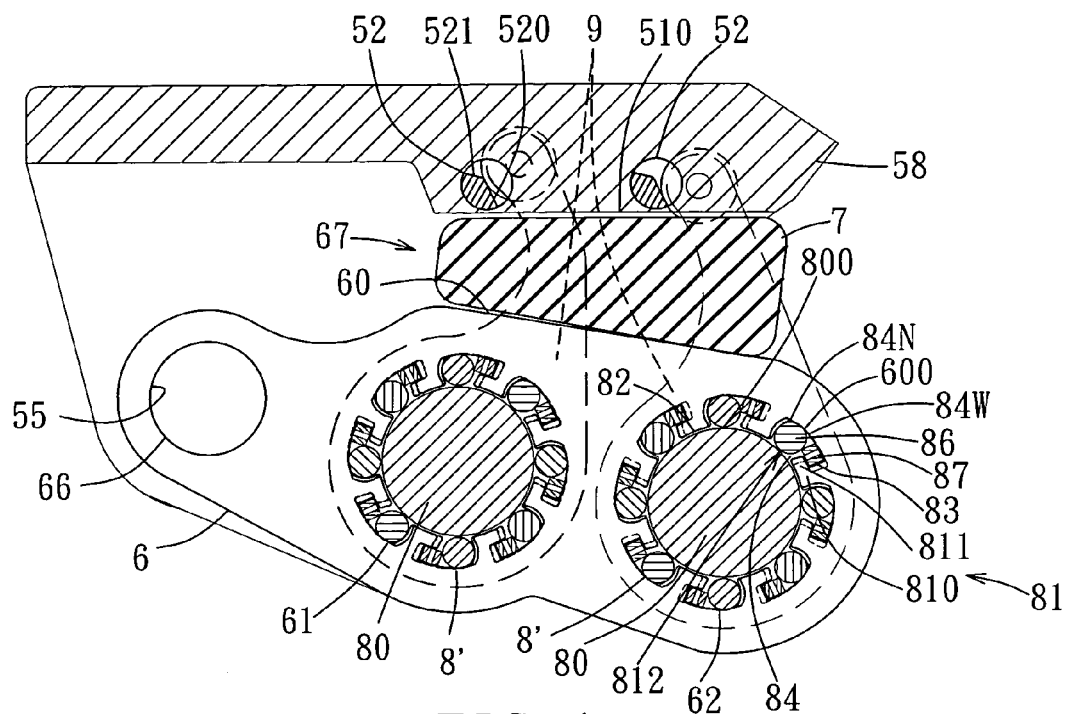
FIG. 4 is a fragmentary, partly sectional schematic view of the preferred embodiment, illustrating the structures of two unidirectional bearings.
Figure 5:
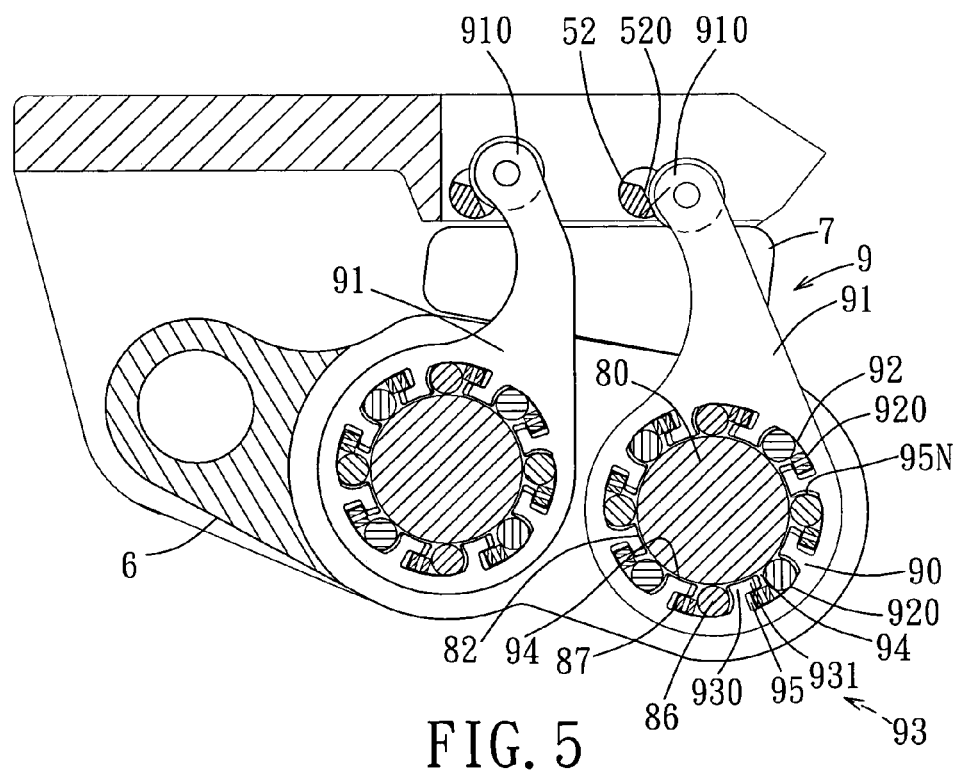
FIG. 5 is a fragmentary, partly sectional schematic view of the preferred embodiment, illustrating engagement between rounded free ends of two pin-locking members and lower planar surfaces of two stop members when the pin-locking members are disposed in pin-releasing positions.

Referring to FIGS. 2, 3, 4, and 5, the preferred embodiment of an artificial knee joint according to this invention is adapted to interconnect a residual thigh 44 and a prosthetic lower leg 45. The artificial knee joint includes a knee seat 5 attached to the thigh 44, a support frame 5' attached to the prosthetic lower leg 45, a driving member 6, two links 63, 64, a cushion device consisting of two rubber blocks 7, a bearing unit 8 consisting of two bearing members in the form of unidirectional bearings 8', and two pin-locking members 9.

The knee seat 5 has a bottom end 50 that is formed with a mounting recess 51. The mounting recess 51 has a top end that is defined by an inner wall surface 510. Two stop members 52 are disposed respectively and fixedly within two parallel holes 57 in the knee seat 5, and extend through an upper end portion of the mounting recess 51. The knee seat 5 further has two opposite side surfaces 53, 54, two pivot holes 55, 56 formed through the knee seat 5 and disposed between the side surfaces 53, 54, and two aligned projections 58 disposed in proximity to the side surface 54.

The driving member 6 is disposed pivotally in the mounting recess 51 by means of a pivot pin 66, and has a top surface 60, and a lock-receiving slot 67 defining two driving portions 68 located to two opposite sides of the slot 67. Each of the driving portions 68 is formed with two mounting holes 61, 62 spaced apart from each other by a predetermined distance.

The links 63, 64 have lower ends connected pivotally to the support frame 5'.

The rubber blocks 7 are disposed in the mounting recess 51 in the knee seat 5 and between the knee seat 5 and the driving member 6, and have bottom surfaces abutting respectively against the driving portions 68 of the driving member 6, and top surfaces abutting against the inner wall surface 510 of the knee seat 5 and the projections 58. As such, the rubber blocks 7 can dampen downward movement of the knee seat 5 relative to the driving member 6.

Two pivot pins 80 extend respectively through the upper ends of the links 63, 64. Each of the pivot pins 80 is journalled within a respective one of the mounting holes 61, 62 in the driving member 6 by a respective one of the unidirectional bearings 8'.

The pin-locking members 9 are sleeved respectively and rotatably on the pivot pins 80. Each of the pin-locking members 9 is rotatable between a pin-releasing position shown in FIGS. 4, 5, and 6 and a pin-locking position shown in FIG. 10.

Each of the unidirectional bearings 8' includes a plurality of angularly equidistant L-shaped projections 81 and a plurality of rollers 86. Each of the L-shaped projections 81 has a radial portion 810 extending inwardly from an annular inner wall surface 600 of the driving member 6 that defines the corresponding mounting hole 61, 62, and a circumferential portion 811 extending perpendicularly from a radial inner end of the radial portion 810. The L-shaped projections 81 cooperate with the inner wall surfaces 600 of the driving member 6 and the rollers 86 to define a plurality of spring-positioning spaces 83 and a plurality of roller-receiving spaces 84. Each of the spring-positioning spaces 83 is disposed between the corresponding L-shaped projection 81 and the corresponding inner wall surface 600 of the driving member 6. Each of the roller-receiving spaces 84 is disposed between the radial portion 810 of the corresponding L-shaped projection 81 and the circumferential portion 811 of an adjacent one of the L-shaped projections 81, and between the corresponding inner wall surface 600 of the driving member 6 and the corresponding pivot pin 80. Each of the roller-receiving spaces 84 has a narrow end (84N) defined by the corresponding radial portion 810, a wide end (84W) defined by the corresponding circumferential portion 811, and a width (i.e., a distance between the corresponding inner wall surface 600 of the driving member 6 and the corresponding pivot pin 80 reducing gradually from the wide end (84W) to the narrow end (84N). The rollers 86 are disposed respectively and movably within the roller-receiving spaces 84. For each of the unidirectional bearings 8', when the rollers 86 are disposed respectively within the narrow ends (84N) of the roller-receiving spaces 84, they are in frictional contact with both the inner wall surface 600 of the driving member 6 and the corresponding pivot pin 80. This prevents rotation of the corresponding pivot pin 80 within the driving member 6 and, thus, relative rotation between the knee seat 5 and the support frame 5'.

Figure 14:
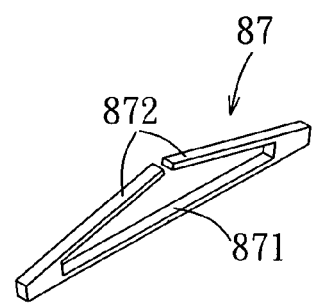
FIG. 14 is a perspective view of a resilient member of the preferred embodiment.

Each of the unidirectional bearings 8' further includes a plurality of unitary resilient members 87 each disposed among the radial portion 810 and the circumferential portion 811 of the corresponding L-shaped projection 81 and the corresponding inner wall surface 600 of the driving member 6. With further reference to FIG. 14, each of the resilient members 87 has an abutment rod portion 871 abutting against the corresponding roller 86, and two resilient arms 872 extending respectively and obliquely from two ends of the abutment rod portion 871 toward each other and forming an angle therebetween. Each of the resilient arms 872 has a portion that is disposed within the corresponding spring-positioning space 83 and that abuts against the corresponding radial portion 810. As such, the resilient members 87 bias respectively the rollers 86 to move toward the narrow ends (84N) of the roller-receiving spaces 84.

The pin-locking members 9 are disposed within the slot 67 in the driving member 6. Each of the pin-locking members 9 has an annular pivot portion 90, a tongue 91 extending upwardly from the pivot portion 90 and having a rounded free end 910, a pivot hole 92 formed in the pivot portion 90 and defined by an annular inner wall surface 920, and a plurality of angularly equidistant L-shaped stop blocks 93 extending from the inner wall surface 920. The pivot pins 80 extend respectively through the pivot holes 92. Each of the L-shaped stop blocks 93 is similar in construction to the L-shaped projections 81, and has a radial portion 930 and a circumferential portion 931 to define a spring-positioning space 94 and a roller-receiving space 95. Each of the roller-receiving spaces 95 has a narrow end (95N) (see FIG. 5) and a wide end (95W) (see FIG. 10). Each of the resilient members 87 extends through the corresponding spring-positioning space 94.

Figure 6:
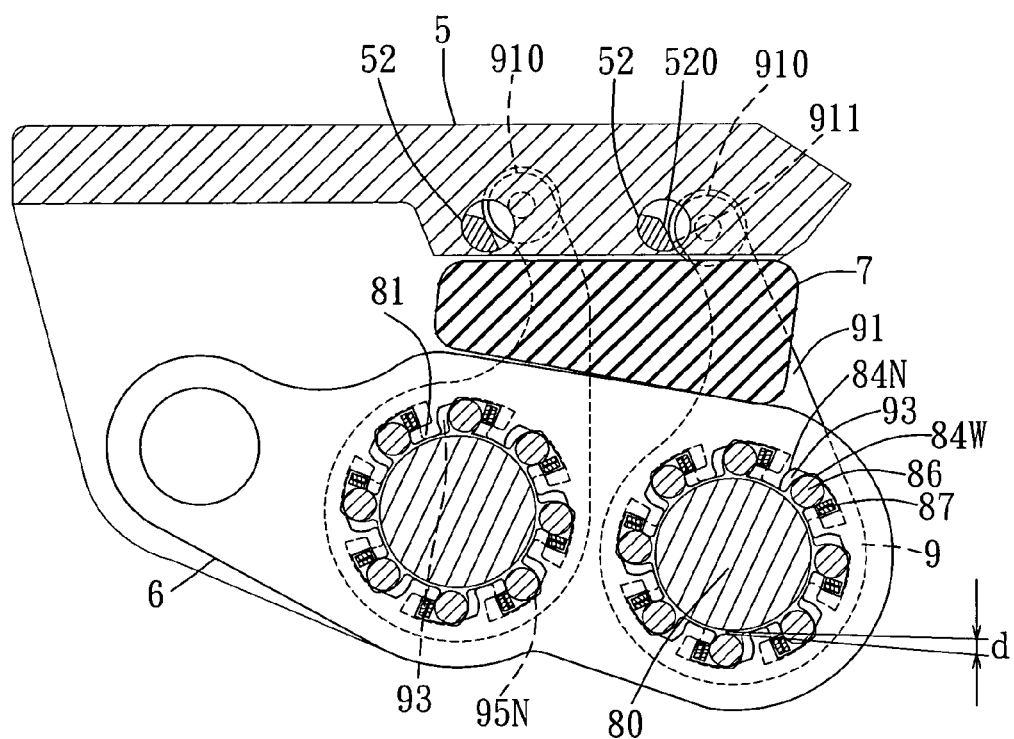
FIG. 6 is a fragmentary, partly sectional schematic view of the preferred embodiment, illustrating how a plurality of rollers are spaced apart from two pivot pins when the pin-locking members are disposed in the pin-releasing positions.

The L-shaped stop blocks 93 are positioned relative to the L-shaped projections 81 such that, when the pin-locking members 9 are disposed in the pin-releasing positions, the rollers 86 are disposed respectively at the narrow ends (95N) of the roller-receiving spaces 95 and the wide ends (84W) of the roller-receiving spaces 84, as shown in FIG. 6. As such, since each of the rollers 86 is spaced apart from the corresponding pivot pin 80 by a distance (d) (see FIG. 6), relative rotation between the knee seat 5 and the support frame 5' is allowed.

Each of the stop members 52 is configured as a rod parallel to the pivot pins 80, and has an upper planar surface 521 and a lower planar surface 520 disposed below and connected to the upper planar surface 521.

Figure 7:
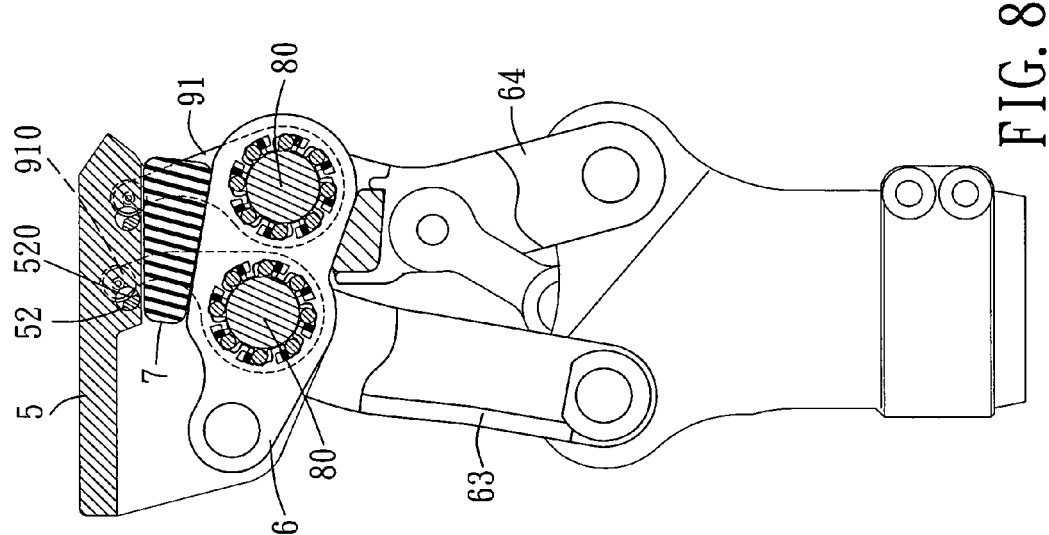
FIG. 7 is a partly sectional schematic side view of the preferred embodiment shown in a state when the user is walking on a horizontal surface and when the joint is flexed.

With additional reference to FIG. 7, when the user walks on a horizontal surface (not shown) and when the artificial knee joint is flexed, the lower planar surfaces 520 of the stop members 52 abut respectively against the rounded free ends 910 of the pin-locking members 9. Therefore, the stop members 52 hold respectively the pin-locking members 9 in the pin-releasing positions, and the pin-locking members 9 confine the rollers 86 within the wide ends (84W) of the roller-receiving spaces 84.

Figure 8:
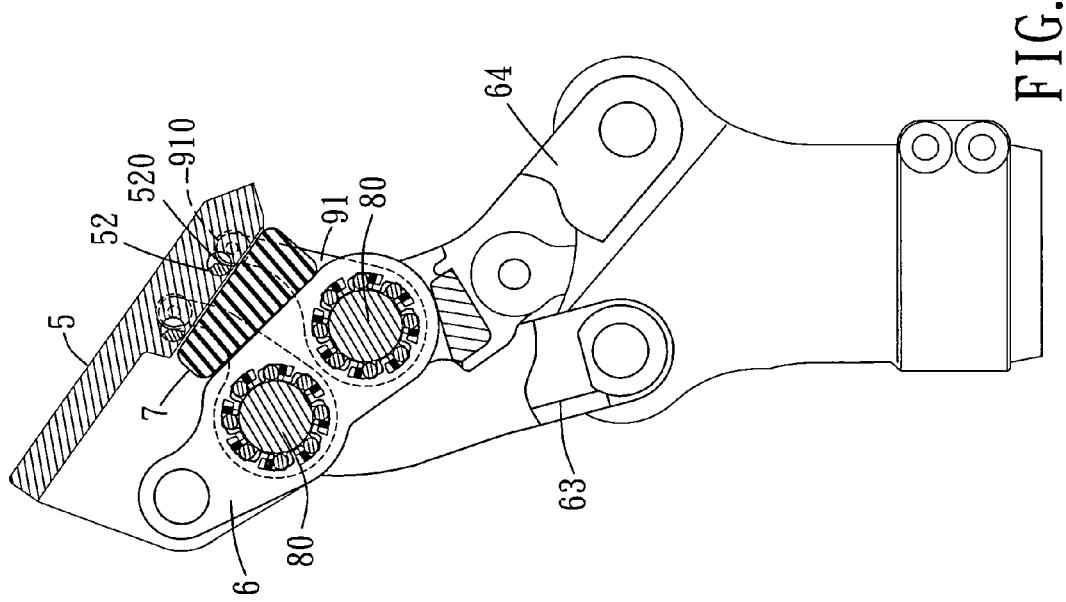
FIG. 8 is a partly sectional schematic side view of the preferred embodiment shown in a state when the user is walking on a horizontal surface and when a residual thigh is aligned with a prosthetic lower leg.

With additional reference to FIG. 8, when the user walks on the horizontal surface and when the residual thigh 44 is aligned with the prosthetic lower leg 45, the lower planar surfaces 520 of the stop members 52 again abut respectively against the rounded free ends 910 of the pin-locking members 9, thereby holding the pin-locking members 9 in the pin-releasing positions.

Figure 9:
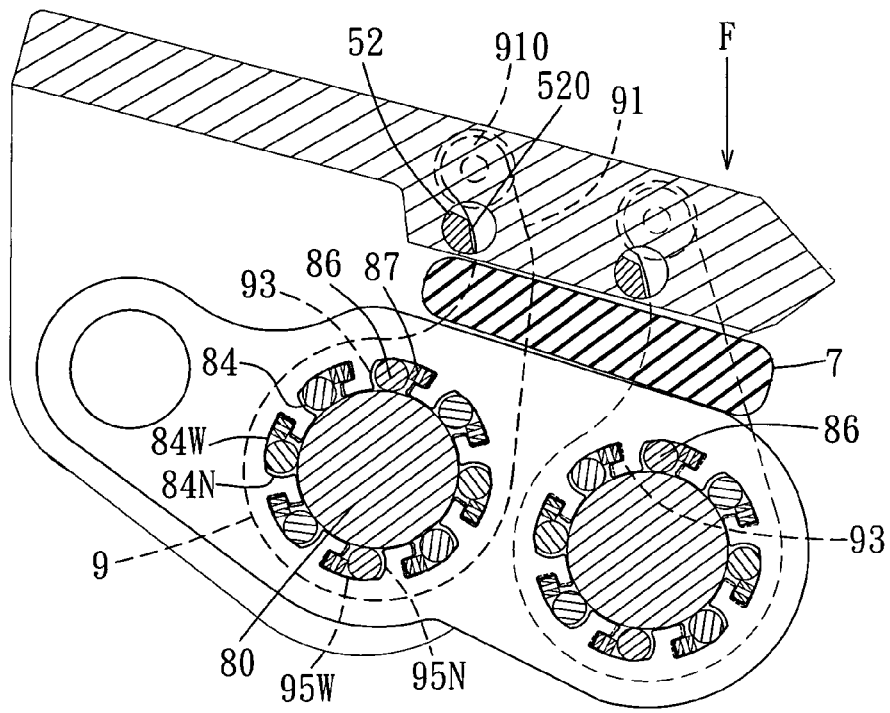
FIG. 9 is a fragmentary, partly sectional schematic side view of the preferred embodiment, illustrating how a downward force is applied to a rear end of a knee seat so as to remove the rounded free ends of the pin-locking members from the lower planar surfaces of the stop members, thereby allowing the rollers to be biased to move from wide ends of roller-receiving spaces toward narrow ends of the roller-receiving spaces.

With additional reference to FIG. 9, when the user walks down a slope (not shown), the weight of the user results in the application of a downward force (F) to a rear end of the knee seat 5. This compresses the rubber blocks 7 so as to allow the stop members 52 to move respectively and downwardly away from the rounded free ends 910 of the pin-locking members 9. When the stop members 52 are removed from the rounded free ends 910 of the pin-locking members 9, frontward pivoting movement of the pin-locking members 9 relative to the driving member 6 is allowed. Hence, the rollers 86 are released respectively from the pin-locking members 9, and therefore are biased by the resilient members 87 to move from the wide ends (84W) of the roller-receiving spaces 845 toward the narrow ends (84N) of the roller-receiving spaces 84.

Figure 10:
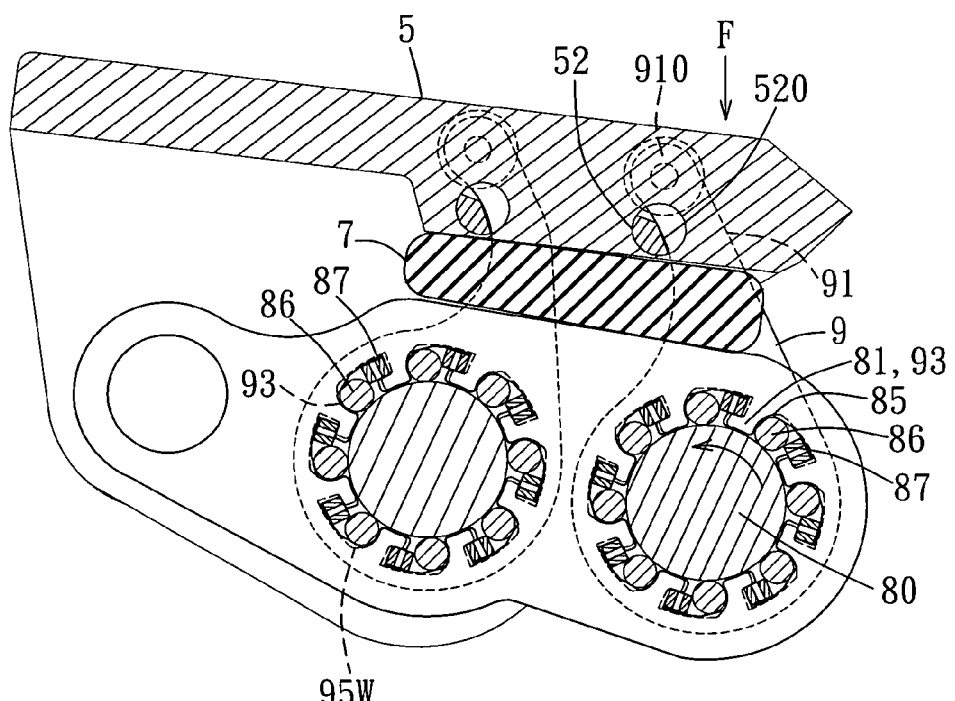
FIG. 10 is a fragmentary, partly sectional schematic side view of the preferred embodiment when each of the rollers is disposed in the narrow end of the corresponding roller-receiving space to contact a pivot pin and an annular inner wall surface of a driving member.

When the center of gravity of the user moves rearwardly and downwardly within a very short time to thereby reduce a knee angle between the knee seat 5 and the support frame 5' and between the residual thigh 44 and the prosthetic lower leg 45 to a threshold angle, the rubber blocks 7 are compressed as shown in FIG. 10, such that the rollers 86 move to the narrow ends (84N) of the roller-receiving spaces 84. As a consequence, the knee angle can be maintained at the threshold angle. That is, the artificial knee joint of this invention has a minimum knee angle. This prevents the user from falling down when instantly shifting his or her center of gravity rearwardly and downwardly. Thus, the object of this invention can be achieved.

Figure 11:
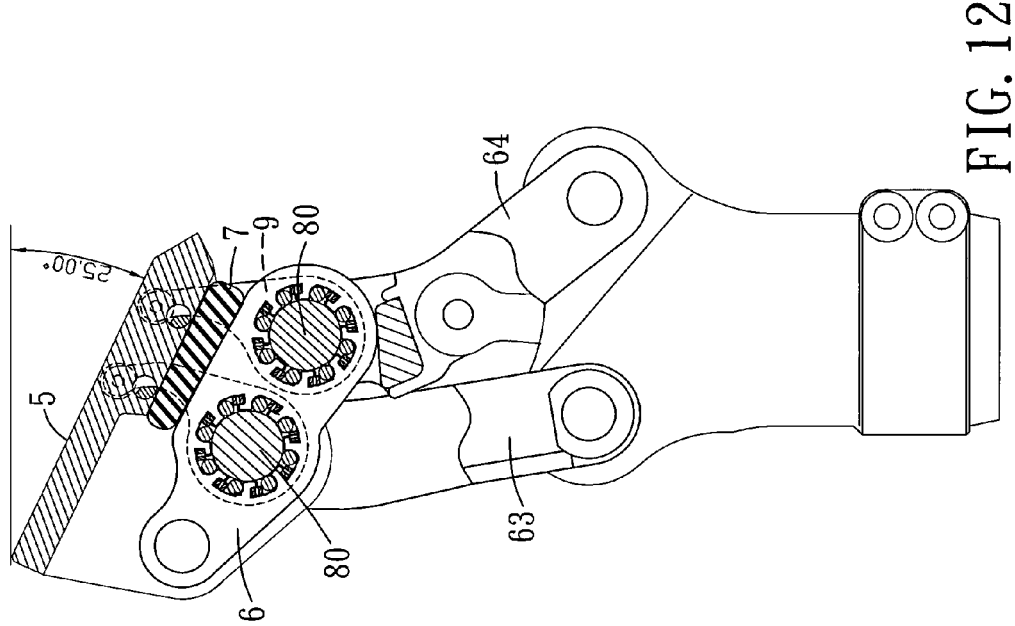
FIG. 11 is a partly sectional schematic side view of the preferred embodiment when a threshold angle is set at 165 degrees.
Figure 12:
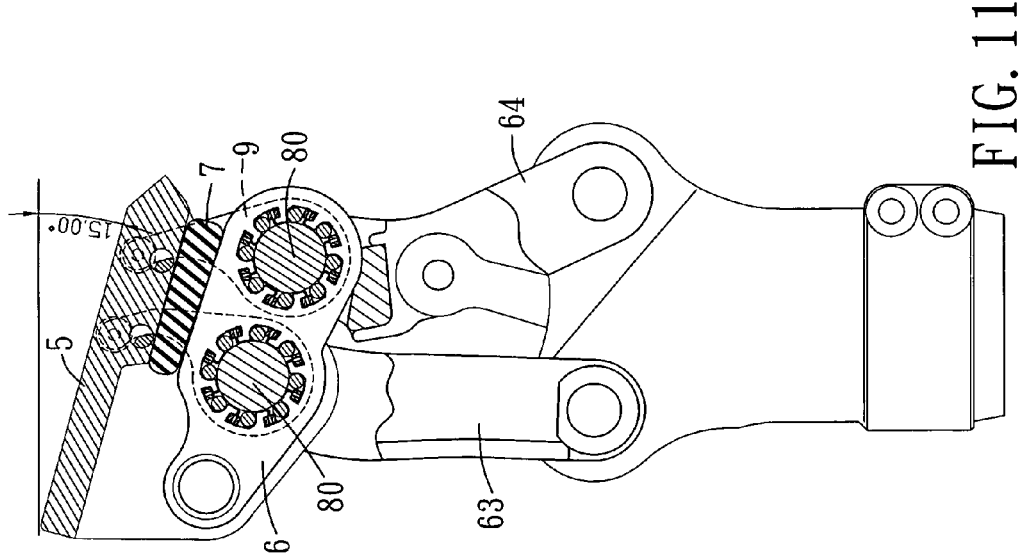
FIG. 12 is a partly sectional schematic side view of the preferred embodiment when the threshold angle is set at 155 degrees.
Figure 13:
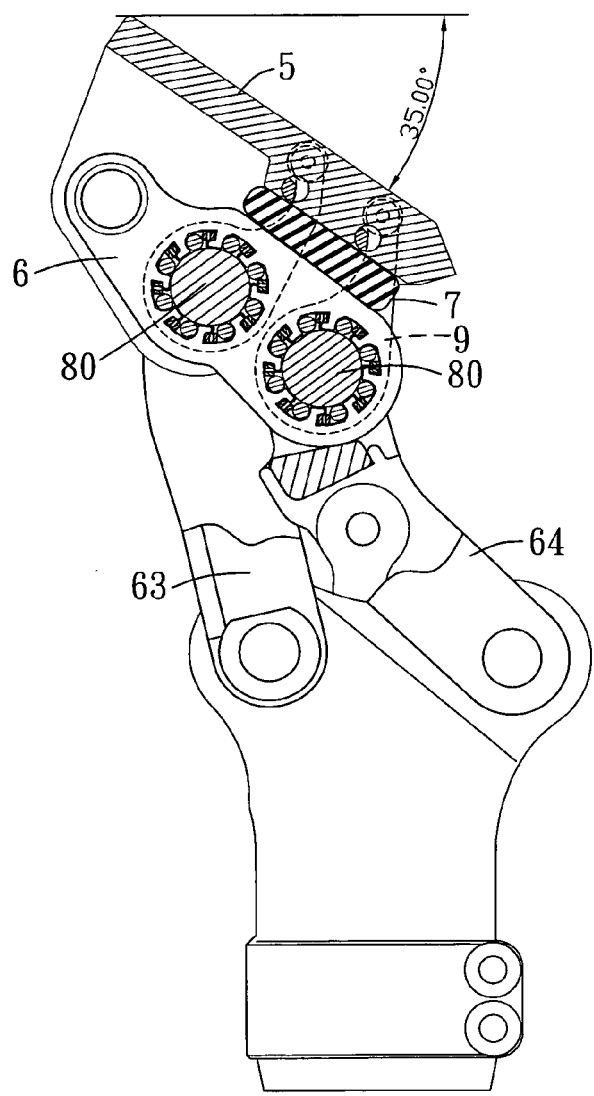
FIG. 13 is a partly sectional schematic side view of the preferred embodiment when the threshold angle is set at 145 degrees.

The threshold angle may be set at 165 degrees (as shown in FIG. 11), 155 degrees (as shown in FIG. 12), or at 145 degrees (as shown in FIG. 13).

With this invention thus explained, it is apparent that numerous modifications and variations can be made without departing from the scope and spirit of this invention. It is therefore intended that this invention be limited only as indicated by the appended claims.

I claim:

1. An artificial knee joint adapted to interconnect a residual thigh and a prosthetic lower leg and comprising:
    a knee seat adapted to be attached to the thigh and having a bottom end that is formed with a mounting recess, said mounting recess having a top end defined by an inner wall surface;
    a support frame adapted to be attached to the prosthetic lower leg;
    a stop member disposed fixedly in an upper end portion of said mounting recess in said knee seat;
    a driving member disposed pivotally in said mounting recess in said knee seat and having two mounting holes spaced apart from each other by a predetermined distance;
    a cushion device disposed between said inner wall surface of said knee seat and said driving member so as to dampen downward movement of said knee seat relative to said support frame;
    two links each having opposite upper and lower ends, each of said lower ends of said links being connected pivotally to the support frame;
    two bearing members, at least one of which is configured as a unidirectional bearing;
    two pivot pins extending respectively through said upper ends of said links, each of said pivot pins being journalled within a respective one of said mounting holes in said driving member by a respective one of said bearing members; and
    a pin-locking member sleeved rotatably on one of said pivot pins and connected to said unidirectional bearing and said stop member, said pin-locking member being held in a pin-releasing position by said stop member so as to allow for rotation of said one of said pivot pins within said driving member and, thus, relative rotation between said knee seat and said support frame when a knee angle between said knee seat and said support frame is greater than a threshold angle, said pin-locking member being released from said stop member and being disposed in a pin-locking position so as to prevent rotation of said one of said pivot pins within said driving member and, thus, relative rotation between said knee seat and said support frame when the knee angle is equal to said threshold angle.

2. The artificial knee joint as claimed in claim 1, wherein said unidirectional bearing includes a plurality of angularly equidistant L-shaped projections and a plurality of rollers, each of said L-shaped projections having a radial portion extending inwardly from an annular inner wall surface that defines a corresponding one of said mounting holes in said driving member, and a circumferential portion extending perpendicularly from a radial inner end of said radial portion, said L-shaped projections cooperating with said inner wall surfaces of said driving member and said one of said pivot pins to define a plurality of roller-receiving spaces, each of which is disposed between said circumferential portion of a corresponding one of said L-shaped projections and said radial portion of an adjacent one of said L-shaped projections and between said annular inner wall surface of said driving member and said one of said pivot pins, each of said roller-receiving spaces having a narrow end defined by a corresponding one of said radial portions, a wide end defined by a corresponding one of said circumferential portions, and a width defined by said annular inner wall surface of said driving member and said one of said pivot pins and reducing gradually from said wide end to said narrow end, said rollers being disposed respectively and movably within said roller-receiving spaces, said rollers being in frictional contact with both said annular inner wall surface of said driving member and said one of said pivot pins so as to prevent rotation of said one of said pivot pins within said driving member and, thus, relative rotation between the thigh and the support frame when said rollers are disposed respectively within said narrow ends of said roller-receiving spaces.

3. The artificial knee joint as claimed in claim 2, wherein said unidirectional bearing further includes a plurality of resilient members each disposed between said circumferential portion of a respective one of said L-shaped projections and said annular inner wall surface of said driving member so as to bias a corresponding one of said rollers to move toward said narrow end of a corresponding one of said roller-receiving spaces.

4. The artificial knee joint as claimed in claim 3, wherein said pin-locking member is formed with a pivot hole for extension of said one of said pivot pins therethrough, said pivot hole being defined by an annular inner wall surface that is formed with a plurality of angularly equidistant L-shaped stop blocks, which confine respectively said rollers within said wide ends of said roller-receiving spaces when said pin-locking member is disposed in said pin-releasing position, and which release respectively said rollers therefrom so as to allow said rollers to be biased by said resilient members to move to said narrow ends of said roller-receiving spaces when said pin-locking member is disposed in said pin-locking position.

5. The artificial knee joint as claimed in claim 4, wherein said pin-locking member has a rounded free end, said stop member being configured as a rod parallel to said pivot pins and having an upper planar surface and a lower planar surface that is disposed below and connected to said upper planar surface, said rounded free end of said pin-locking member abutting against said lower planar surface of said stop member so as to prevent pivoting movement of said pin-locking member relative to said driving member and, thus, movement of said rollers from said wide ends of said roller-receiving spaces to said narrow ends of said roller-receiving spaces when said pin-locking member is disposed in said pin-releasing position, said upper planar surface of said stop member being removable from said rounded free end of said pin-locking member so as to allow for pivoting movement of said pin-locking member from said pin-releasing position to said pin-locking position, thereby permitting said rollers to be biased by said resilient members to move from said wide ends of said roller-receiving spaces to said narrow ends of said roller-receiving spaces.

6. The artificial knee joint as claimed in claim 5, wherein said cushion device includes a rubber block, application of a rearward force to a rear end of said knee seat resulting in compression of said rubber block so as to release said rounded free end of said pin-locking member from said lower planar surface of said stop member, thereby allowing said resilient members to bias said rollers from said wide ends of said roller-receiving spaces toward said narrow ends of said roller-receiving spaces.

* * * * *